United States Patent [19]

Wood

[11] Patent Number: 5,531,732
[45] Date of Patent: Jul. 2, 1996

[54] ADJUSTABLE FIT DISPOSABLE TRAINING PANT OR INCONTINENCE GARMENT HAVING DISPOSABLE MEANS

[75] Inventor: Leigh E. Wood, Woodbury, Minn.

[73] Assignee: Minnesota Mining and Manufacturing Company, St. Paul, Minn.

[21] Appl. No.: 259,525

[22] Filed: Jun. 14, 1994

[51] Int. Cl.⁶ .................................................. A61F 13/15
[52] U.S. Cl. ........................ 604/391; 604/393; 604/396; 604/385.2
[58] Field of Search .................. 604/385.2, 391–398

[56] References Cited

U.S. PATENT DOCUMENTS

| | | | |
|---|---|---|---|
| 4,938,753 | 7/1990 | Van Gompel et al. | 604/385.2 |
| 4,938,757 | 7/1990 | Van Gompel et al. | 604/396 |
| 4,940,464 | 7/1990 | Van Gompel et al. | 604/396 |
| 5,163,932 | 11/1992 | Nomura et al. | 604/385.2 |
| 5,171,439 | 12/1992 | Vakharia | 210/172 |
| 5,188,627 | 2/1993 | Igaue et al. | 604/385.2 |
| 5,242,436 | 9/1993 | Weil et al. | 604/385.2 |
| 5,246,433 | 9/1993 | Hasse et al. | 604/396 |
| 5,370,634 | 12/1994 | Ando et al. | 604/396 |

FOREIGN PATENT DOCUMENTS

| | | |
|---|---|---|
| 0374730A2 | 6/1990 | European Pat. Off. . |
| 0526868A2 | 2/1993 | European Pat. Off. . |
| 0529681A1 | 3/1993 | European Pat. Off. . |
| 0547497A2 | 6/1993 | European Pat. Off. . |
| 0570980A1 | 11/1993 | European Pat. Off. . |
| WO94/00292 | 1/1994 | WIPO . |

*Primary Examiner*—Robert A. H. Clarke
*Attorney, Agent, or Firm*—Gary L. Griswold; Walter N. Kirn; William J. Bond

[57] ABSTRACT

A disposable training pant is provided with a mechanical fastening tab permanently sealed to a fibrous web in the side panel portion at a first end. The second end of the mechanical fastening tab is free to adhere to the same or another fibrous web for adjustment of fit and disposability. The first end of the mechanical fastening tab is heat sealed, interlocking the male mechanical fastening element to the fibers of the fibrous web.

20 Claims, 3 Drawing Sheets

ADJUSTABLE FIT DISPOSABLE TRAINING PANT OR INCONTINENCE GARMENT HAVING DISPOSABLE MEANS

BACKGROUND AND FIELD OF INVENTION

The present invention relates to a disposable training pant or incontinent garment where improved fit and adjustability is provided. Specifically, the invention relates to disposable training pants for a child or adult incontinent articles. Generally these incontinent articles or training pants have elasticated side panels with woven or nonwoven fibrous layers provided on the outer and/or inner faces of the elastic side panels.

Conventional baby diapers and some adult incontinent products are produced with adjustable adhesive closure systems provided on opposing ears or corner portions of the garment. These closure systems comprise a pressure sensitive adhesive fastening tab permanently attached to one garment ear at one end of the fastening tab with a fastening tab free end stored on a release tape or film prior to use. The fastening tab is permanently attached at one end of the diaper and the fastening tab free end releasably secures to an opposing end of the diaper when in use. The diaper opposing end, generally the front end, is often provided with a reinforcement strip or tape on the inner or outer face of an outer liquid-impermeable back sheet where the fastening tab free end adheres. The back sheet is conventionally a thin polyethylene polymer or copolymer film. As the adhesive fastening tab free end can be placed across the entire front end of the diaper the diaper waist opening is easily adjusted to the individual wearer.

When training the child to use a toilet, traditionally, a training pant is used. This training pant is generally a cloth garment provided with absorbent fabric and is used in combination with a rubber outer pant, or the like. Recently, disposable training pants have become popular. However, these disposable training pants lack the adjustability of a conventional diaper adhesive fastening tab closure system.

Slight adjustability in fit or size have been obtained by extensive use of elastics in disposable training pants. The elastics are used, for example; in the leg regions; in the waist regions; along the side panel portions of the training pants, as disclosed in U.S. Pat. No. 4,938,753 (van Gompel et al.)—elasticized stretchable side panels; U.S. Pat. No. 5,246,433 (Hasse et al.)—elasticated ear flaps; European Patent 547 497 A2 (van Gompel et al.)—elastic side panels having a gradient stretch or elastic bands in the side panels; elasticated waist and leg openings—elasticated waist and leg openings; European Patent 526 868 A2—elastic front ear portions or U.S. Pat. No. 5,163,932 (Nomura et al.)—elasticated waist and leg regions. Others patents describing the use of elastics include U.S. Pat. Nos. 4,940,464; 4,938,757; 5,171,439; and 5,188,627. The difficulty with these designs rests in the limited adjustability provided by elastics regardless of placement (be it in the waist, leg, side panel region or a combination thereof) or the extent to which elastic is used in the training pants. Although generally the more elastic used the more adjustable the fit or size there are limits. Generally improvements in adjustability of fit diminish with increasing use of elastic in a training pant design. Further using increased levels of elastic in a disposable training pant also increases manufacturing complexity and cost.

The present invention seeks to provide a disposable training pant with increased adjustability in fit or size beyond that obtainable with elastics.

SUMMARY OF THE INVENTION

According to the present invention, a disposable training pant is provided having a fibrous outer web which can engage with male mechanical fastening elements on a mechanical fastening tab. The mechanical fastening tab is located on a seam or side panel portion of the training pant such that a free end of the mechanical fastening tab is able to engage the woven or nonwoven outer cover web. The mechanical fastening tab free end adjusts the training pant circumferential or waist fit or size by gathering the side panel portion. The side panel portion is gatherable at least in part by being free of any integrally bonded absorbent core structure.

Preferably, a permanent bond end of the mechanical fastening tab is heat sealed to a fibrous outer web, or an inner liquid permeable topsheet or another fibrous web. This heat sealing permanently bonds or locks at least some of the male mechanical fastening elements of the mechanical fastening tab to fibers of the outer web, topsheet or other web.

In a further preferred embodiment the mechanical fastening tab free end is also subsequently usable as a disposal means when the training pant is removed from the wearer, e.g., by tearing the side panel. The fastening tab remains on the training pant side panel portion. The training pant is then rolled into a compact form for disposal and the mechanical fastening tab is used to keep the training pant in a rolled form.

DESCRIPTION OF THE PREFERRED EMBODIMENTS

The mechanical fastening tab constructions of the present invention will be described with reference to disposable training pants, however, the constructions would be equally applicable to other like disposable garments and incontinent devices.

Figure 1:
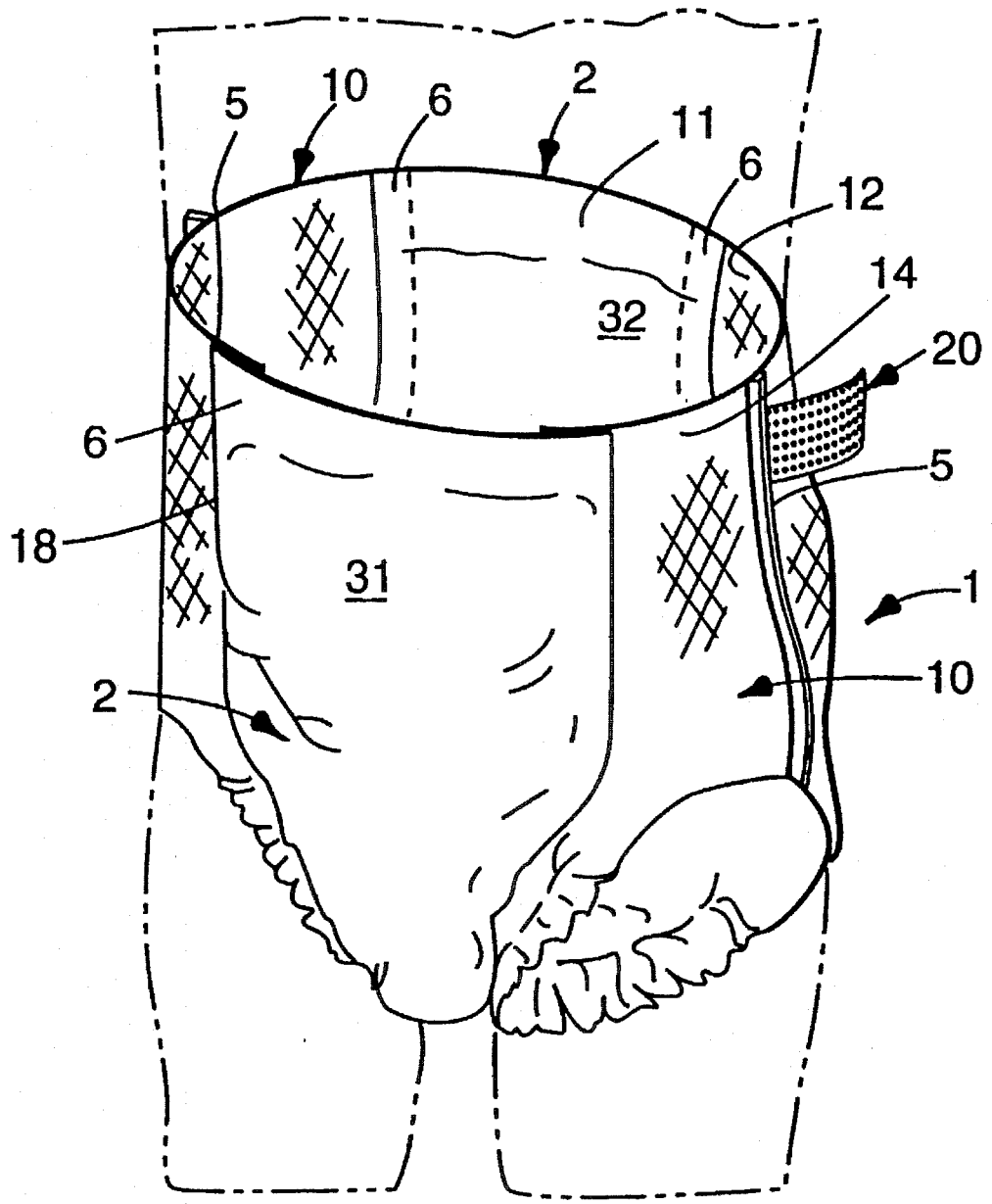
FIG. 1 is a perspective view of a first disposable training pant embodiment of the present invention where a mechanical fastening tab is placed adjacent a side seam.
Figure 2:
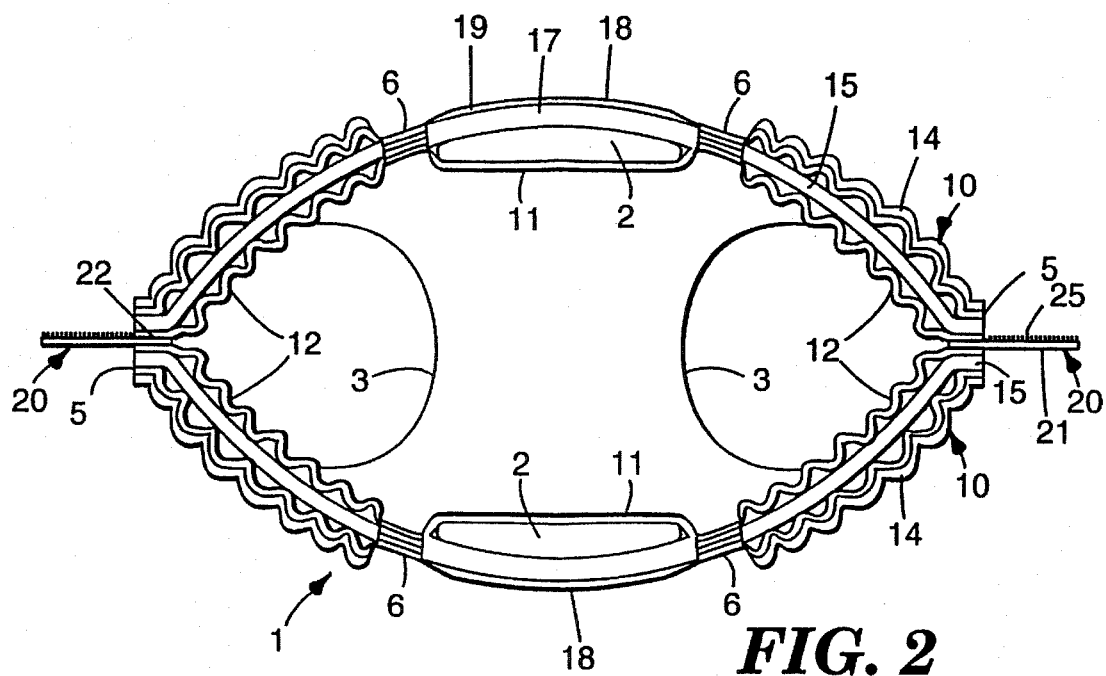
FIG. 2 is a top view of a training pant of the present invention having a mechanical fastening tab located within the side seam.

A known disposable training pant is depicted in FIGS. 1 and 2, where the training pant chassis (1) is formed into an absorbent core (2) containing portion and side panel portions (10) designed to fit around the hip of the wearer. The side panel portions (10) with the absorbent core define leg openings in the training pant chassis.

The absorbent core (2) structure would be of conventional design, such as disclosed, for example, in U.S. Pat. No. 5,246,433, utilizing absorbent fibers and/or particulates in the form of a discrete pad. The pad is covered on an inner face by a liquid-permeable topsheet (11) and on the outer face by a liquid-impermeable outer layer (18). The liquid-permeable topsheet (11) can cover the absorbent core (2) and extend continuously into the side panel portions (10), as shown in FIG. 2, or be attached to the side panel portions (10) by a seam (not shown). Similarly, the liquid-impermeable outer layer (18) can extend beyond the absorbent core (2) portion into the side panel portions (10), as shown in FIG. 2, or be attached by a seam (6) to a discrete side panel portion (10).

In a preferred arrangement, as shown in FIG. 2, the liquid-impermeable outer layer (18) is a laminate comprising a liquid-impermeable inner layer (17) laminated to an outer layer (19) of a fibrous web. Inner layer (17) would preferably be a liquid-impermeable plastic film such as a polyethylene or polypropylene film or a consolidated woven or nonwoven web. The outer layer (19) is preferably a soft woven (including knitted or stitchbonded webs) or nonwoven web, such as a melt blown, spun bond, carded, or otherwise formed nonwoven web, formed of synthetic and/or natural fibers. Preferably, fibrous web (19) is sufficiently coherent and lofty, such that fibers of the web (19) are spaced sufficiently far apart from each other and the backing such that the fibers are engagable with the mechanical fastening tab free end male mechanical fastening elements.

The liquid-permeable topsheet (11) is of conventional design as used in disposable diapers and generally would be a spun bond web of hydrophobic thermoplastic fibers (i.e., polypropylene fibers). The backsheet and topsheet layers (11 and 18) are joined to each other and the absorbent pad by conventional lamination techniques including the use of hot melt adhesives, thermal bonding, sonic bonding and the like.

The side panel portions (10) can be integral with the front panel (31) of the absorbent core (2) portion and/or the rear panel (32) portion of the absorbent core (2) portion or are joined to each other by a side seam (5), such as shown in FIG. 2.

Alternatively, the side panels (10) can be integral with either just the front panel (31) or just the rear panel (32) and extend to the opposing rear or front panel and joined to the opposing panel by adhesion, welding, or the like, such as disclosed in PCT 94/00292, published Jan. 6, 1994.

In a further alternative shown in FIG. 1, side panels (10) are attached at seams (6) to both the front panel (31) and the back panel (32) with an intermediate seam (5). Intermediate seam (5) in this arrangement could be eliminated, by using a single side panel element, however preferably, intermediate seam (5) is use to facilitate manufacture of the training pant, such as disclosed in U.S. Pat. Nos. 4,938,757 or 5,246,433 and incorporation of the mechanical fastening tab (20) into the seam (5).

Side panels (10) can be elastic or inelastic, however, preferably are elastic, such as by incorporation of an elastomeric layer (15) to facilitate fit. The elastomeric layer (15) can be any conventional elastomeric woven or nonwoven web comprising elastomeric fibers such as melt blown fibers, spun bond fibers, extruded fibers, or the like, or an elastomeric film or coextruded elastomeric film. At least the inner or outer face of the side panels are (10) provided with a fibrous woven or nonwoven web, (12) or (14), engagable with the male mechanical fastening elements (25) on the mechanical fastening tab (20).

The mechanical fastening tab (20) has an array of upstanding male mechanical fastening elements (25), which can be in the form of upstanding stems having fiber engaging structures at the distal end, which fiber engaging structures have a shape suitable for engaging fibers. Preferably, the male mechanical fastening elements would be in the form of upstanding hook or mushroom type structures. The elements (25) generally are 75 to 500 microns high from the stem base to the outer tip of the fiber engaging structures. The stems, other than the distal end fiber engaging structure, would generally be free of fiber engaging structures or protrusions and be straight or taper inward from the stem base to the distal end fiber engaging structure. The distal end fiber engaging structures would generally extend outwardly, preferably outwardly and downwardly, from the stem by a distance at least 1 times the average engaged fiber width.

At a manufacturers end (22), the mechanical fastening tab (20) is permanently bonded to the inner topsheet (11) extension, the inner fibrous web (12) or the outer fibrous web (14). The male mechanical fastening elements (25) on the opposing free end (21) remain free to releasably engage an outer fibrous web (14), outer fibrous web layer (19) or a discrete mating mechanical fastener element attached to a side panel (10) or the front panel (31). This mating mechanical fastener element will also be a fibrous web, such as a woven (including stitchbonded and knitted webs) or nonwoven web where the fibers are sufficiently coherent and lofty (e.g., fibrous loops or an open fibrous structure) to engage the male mechanical fastening elements. The mating mechanical fastener element can extend across the entire side panel and/or front panel or rear panel or only a portion of the side panel or front panel or rear panel rear panel, or or a combination thereof.

The permanent bond at the manufacturers bond end (22) is preferably formed by male mechanical fastening elements (25) securely engaging the fibers of the topsheet or a fibrous web (12, 14, 19 or mating mechanical fastening element). This secure engagement is preferably created by locking the mechanical fastening elements around and between the fibers of the topsheet or fibrous web, using heat welding, pressure welding, ultrasonic welding, mechanical welding, or the like, however an adhesive could also be employed. In this manner, certain of the mechanical fastening elements (25) permanently anchor the fastening tab (20) to at least one panel while other mechanical fastening elements (25) on the fastening tab (20) free end (21) remain undeformed for releasably engaging the fibers of an outer fibrous web (14 or 19) or a suitably placed mating mechanical fastening element.

Figure 6:
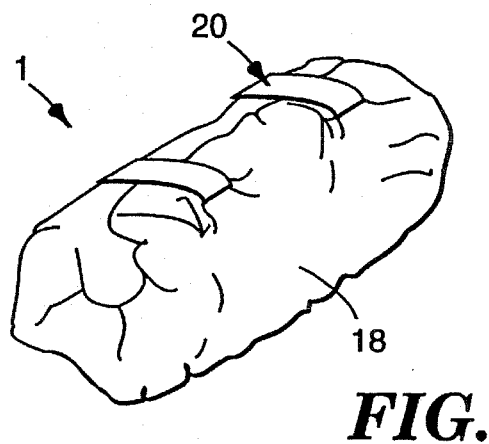
FIG. 6 is a perspective view of a training pant according to the invention in a folded or rolled condition for disposal.

Mechanical fastening tab (20) allows wide adjustments to the fit or size of the training pant (1) by gathering excess side panel material between the permanently attached manufacturers end (22) and the user placed free end (21). The fit can also be adjusted after wear to gather excess material created due to elastic hysteresis or cold stretching of the side panels (10) or absorbent core structure (2) of the training pant chassis (1). Either one or more mechanical fastening tabs (20) can be placed on or adjacent each side panel (10), with the mechanical fastening tabs (20) placeable on one or both sides of the training pant (1). When the training pant (1) is ready for disposal, the mechanical fastening tab (20) can be used to maintain the training pant in a rolled or folded form, as shown in FIG. 6, by suitable placement of the free end (21) of the mechanical fastening tab (20) where the manufacturers end (22) remains permanently attached to one panel (10).

Figure 3:
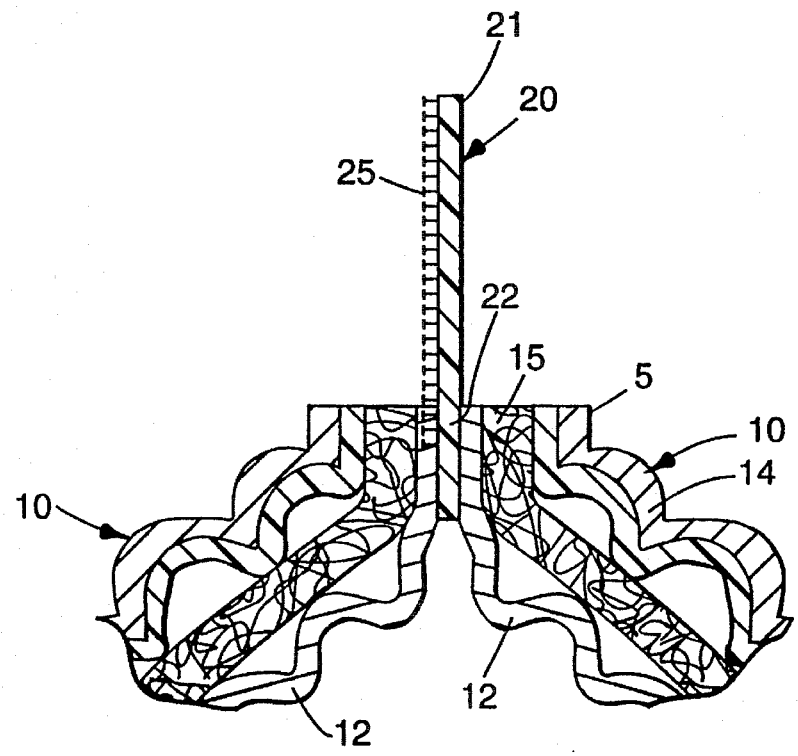
FIG. 3 is a fragmentary sectional view of the embodiment shown in FIG. 2.

FIG. 3 shows a preferred embodiment for placement of the fastening tab (20) between adjacent side panels (10) connected by a seam (5), such as shown in FIG. 1. Although in FIG. 1 this seam (5) is shown provided equidistantly between the front and rear panels (31) and (32) of the absorbent pad (2) structure, the seam (5) can be placed at any location, and one or more seams can be provided depending on the number and type of side panels (10). For example, in European Patent Application No. 320 989, an intermediary break-away inelastic side panel is provided between two elastic side panels providing at least two seams and three side panels intermediary the front and rear panels (31) and (32) of the absorbent core (2) structure. The side panels (10) are joined along seam (5) by use of heat, pressure, ultrasonics, or the like, which preferably simultaneously permanently engages the male mechanical fastening elements (25) on manufacturers end (22) with the fibers of the inner fibrous web (12) or a topsheet extension. If the side seam (5) is subsequently torn, in order to remove the training pant, the mechanical fastening tab (20) will remain permanently attached to one panel element (10) by the fastening elements (25) on manufacturers end (22), suitably releasing from the opposing panel element (10) on the opposite face of the tab along side seam (5).

Figure 4:
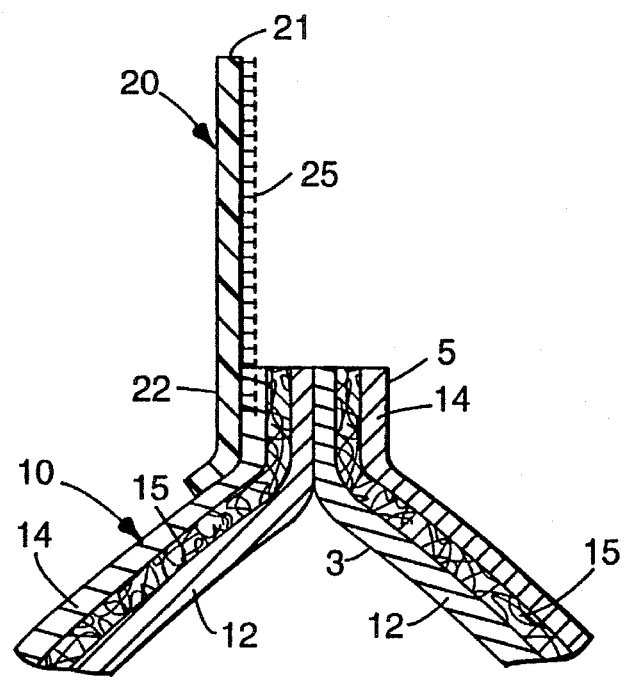
FIG. 4 is a fragmentary sectional view of a second alternative embodiment for placement of the mechanical fastening tab.

In the alternative embodiment of FIG. 4, the mechanical fastening tab (20) is permanently bonded to the outer fibrous web (14) on a side panel (10). Alternatively, the outer fibrous web could be web 19 or a mating mechanical fastening element. Preferably, the permanent bond is formed simultaneously with the formation of the side seam (5), however, this permanent bond can be created before or after formation of the side seam (5). Mechanical inter-locking of the fastening elements (25) at manufacturer's end (22) with the fibers of web (14) keep the fastening tab (20) temporarily in place prior to formation of the permanent bond through the application of heat, pressure, ultrasonics, or the like, to permanently lock at least some of the fastening elements (25) with the fibers of web (14).

Figure 5:
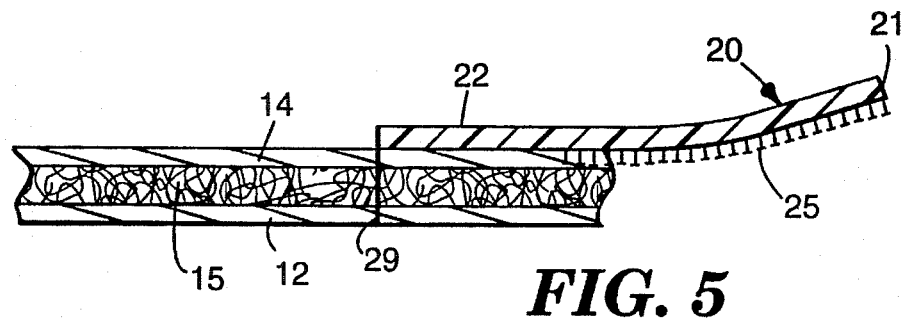
FIG. 5 is a fragmentary sectional view of a third alternative embodiment for placement of a mechanical fastening tab adjacent a welded seam portion.

In the embodiment shown in FIG. 5, the mechanical fastening tab (20) is bonded at manufacturers end (22) to a face of a side panel (10) having an outer fibrous web (14). FIG. 5 shows the presence of a welded side seam (29), which can be formed in the manner described in U.S. Pat. No. 5,246,433.

As is clear from the above description, the invention training pant design allows wide adjustments in fit and size, by a suitable gathering of side panel material between a permanently attached manufacturers end (22) and a free end (21) of a mechanical fastening tab (20). The permanent bond at end (22) can be created without the necessity of adhesive, although such certainly could be employed, and is easily integrated into known manufacturing schemes which employ heat, ultrasonics, or pressure to form side seams for disposable training pants.

Various modifications and alterations of this invention will be apparent to those skilled in the art without departing from the scope and spirit of the invention, and this invention should not be restricted to that set forth for illustrative purposes only.

I claim:

1. A disposable training pant comprising an absorbent core structure formed by an absorbent pad with a liquid-permeable topsheet covering one face and a liquid-impermeable outer layer covering the opposing face of the absorbent pad, at least two side panel portions joining a front panel and a rear panel of the absorbent core structure so as to form a waist opening and two leg openings, at least one mechanical fastening tab, having male mechanical fastening elements on at least one face, said mechanical fastening tab male mechanical fastening elements permanently bonded to at least one panel portion at a manufacturers bond end, mechanical fastening elements on a free end of the mechanical fastening tab being releasably engagable with a first fibrous web on the outer face of the disposable training pant, wherein by placement of the free end of the mechanical fastening tab on the outer face fibrous web, said side panel portion can be gathered between the manufacturers bond end and the free end of the mechanical fastening tab.

2. The disposable training pant of claim 1 wherein the male mechanical fastening element comprises a stem with an enlarged fiber engaging structure at the stem distal end.

3. The disposable training pant of claim 2 wherein the male mechanical fastening element enlarged fiber engaging structure is a hook-like structure.

4. The disposable training pant of claim 1 wherein the male mechanical fastening element enlarged fiber engaging structure is a mushroom-like structure.

5. The disposable training pant of claim 1 wherein said manufacturers bond end male mechanical fastening elements are welded to the fibers of said first fibrous web.

6. The disposable training pant of claim 1 wherein said manufacturers bond end male mechanical fastening elements are attached to said first fibrous web at a first seam between at least one side panel portion and an adjacent panel.

7. The disposable training pant of claim 6 wherein said first seam is between said at least one side panel portion and an adjacent side panel.

8. The disposable training pant of claim 6 wherein said first seam is between said at least one side panel portion and a front or rear panel of the diaper absorbent core structure.

9. The disposable training pant of claim 6 wherein said manufacturers bond end mechanical fastening elements are attached to a second fibrous web on an inner face of said at least one side panel portion.

10. The disposable training pant of claim 9 wherein said second fibrous web on the outer face of said at least one side panel portion is a nonwoven fibrous web.

11. The disposable training pant of claim 6 wherein said manufacturers bond end mechanical fastening elements are attached to a second fibrous web on an outer face of said at least one side panel portion.

12. The disposable training pant of claim 11 wherein said second fibrous web on the outer face of said at least one side panel portion is a nonwoven fibrous web.

13. The disposable training pant of claim 1 wherein the manufacturers bond end is attached to a second fibrous web on the outer face of at least one side panel portion.

14. The disposable training pant of claim 13 wherein said second fibrous web on the outer face of said at least one side panel portion is a nonwoven fibrous web.

15. The disposable training pant of claim 1 having at least one elastic side panel.

16. The disposable training pant of claim 1 wherein the manufacturers bond end is bonded to the at least one panel portion at least by engagement of the male mechanical fastening elements on said manufacturers bond end with fibers of a second fibrous web on the inner or outer face of said at least one panel portion.

17. The disposable training pant of claim 1 wherein the first fibrous web is on an outer face of an adjacent panel.

18. The disposable training pant of claim 17 wherein the first fibrous web is a nonwoven fibrous web.

19. The disposable training pant of claim 17 wherein the first fibrous web is a knitted or woven fibrous web having fibrous loops.

20. The disposable training pant of claim 19 wherein the knitted or woven fibrous web is laminated to at least a portion of said liquid impermeable outer backsheet layer which backsheet layer comprises a liquid impermeable thermoplastic film.

* * * * *